(12) United States Patent
Croft

(10) Patent No.: US 10,784,920 B2
(45) Date of Patent: Sep. 22, 2020

(54) WIRELESSLY DETECTABLE OBJECT THAT EMITS A VARIABLE-FREQUENCY RESPONSE SIGNAL, AND METHOD AND SYSTEM FOR DETECTING AND LOCATING SAME

(71) Applicant: Covidien LP, Mansfield, MA (US)

(72) Inventor: Richard L. Croft, Mead, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/560,300

(22) Filed: Sep. 4, 2019

(65) Prior Publication Data

US 2020/0112332 A1 Apr. 9, 2020

Related U.S. Application Data

(60) Provisional application No. 62/741,274, filed on Oct. 4, 2018.

(51) Int. Cl.
*H04B 1/59* (2006.01)
*H04B 5/00* (2006.01)

(52) U.S. Cl.
CPC .............. *H04B 1/59* (2013.01); *H04B 5/0081* (2013.01)

(58) Field of Classification Search
CPC ................................ H04B 1/59; H04B 1/0081
USPC ................................................ 455/41.1–41.3
See application file for complete search history.

(56) References Cited

U.S. PATENT DOCUMENTS

| | | | |
|---|---|---|---|
| 3,218,638 A * | 11/1965 | Honig .................... | H01Q 21/24 342/50 |
| 5,065,137 A * | 11/1991 | Herman ................ | G08B 13/242 340/572.2 |
| 6,026,818 A | 2/2000 | Blair et al. | |
| 7,696,877 B2 | 4/2010 | Barnes et al. | |
| 7,898,420 B2 | 3/2011 | Blair et al. | |
| 8,111,162 B2 | 2/2012 | Barnes et al. | |
| 8,354,931 B2 | 1/2013 | Blair | |

(Continued)

FOREIGN PATENT DOCUMENTS

EP 2538420 A1 12/2012

OTHER PUBLICATIONS

Extended European Search Report issued in corresponding European Application No. 19201234.2 dated Apr. 21, 2020 (7 pages).

*Primary Examiner* — Yuwen Pan
*Assistant Examiner* — Angelica M Perez
(74) *Attorney, Agent, or Firm* — Carter, DeLuca & Farrell LLP

(57) ABSTRACT

Methods and apparatus are disclosed for detecting a wirelessly detectable object. The wirelessly detectable object may include an antenna and a passive variable-frequency transponder circuit that is communicatively coupled to the antenna. The passive variable-frequency transponder circuit is powered by an interrogation signal received from an external source, and returns via the antenna a wireless response signal having a frequency that varies over a single interrogation cycle. Such variation may be based upon a decaying control voltage that controls the value(s) of one or more components in the passive variable-frequency transponder circuit and/or a switch that selectively couples and decouples components in the passive variable-frequency transponder circuit. The variable frequency may provide a characteristic signature for the wireless response signal that may be used to identify the wirelessly detectable object.

7 Claims, 6 Drawing Sheets

(56) References Cited

U.S. PATENT DOCUMENTS

| | | |
|---|---|---|
| 8,358,212 B2 | 1/2013 | Blair |
| 8,710,957 B2 | 4/2014 | Blair et al. |
| 9,514,341 B2 | 12/2016 | Blair et al. |
| 9,592,962 B1 | 3/2017 | Lee |
| 9,690,963 B2 | 6/2017 | Buhler et al. |
| 9,717,565 B2 | 8/2017 | Blair |
| 9,872,732 B2 | 1/2018 | Blair |
| 10,193,209 B2 | 1/2019 | Blair |
| 2004/0250819 A1 | 12/2004 | Blair et al. |
| 2007/0126582 A1 | 6/2007 | Posamentier |
| 2009/0207037 A1* | 8/2009 | Wiberg ............. G06K 19/0705 340/693.3 |
| 2009/0284352 A1 | 11/2009 | Witschnig et al. |
| 2010/0108079 A1 | 5/2010 | Blair |
| 2010/0109848 A1 | 5/2010 | Blair et al. |
| 2011/0004276 A1 | 1/2011 | Blair et al. |
| 2011/0181394 A1* | 7/2011 | Blair .................... A61B 90/98 340/10.1 |
| 2012/0212330 A1 | 8/2012 | Halberthal et al. |
| 2013/0016021 A1 | 1/2013 | Blair |
| 2016/0204740 A1* | 7/2016 | Trotta .................. H03B 5/1209 331/108 R |
| 2016/0210548 A1 | 7/2016 | Blair |
| 2016/0365890 A1 | 12/2016 | Reynolds et al. |
| 2017/0158165 A1* | 6/2017 | Simons ............ B60R 25/02105 |
| 2017/0169172 A1 | 6/2017 | Blair et al. |
| 2019/0290392 A1 | 9/2019 | Hansen et al. |
| 2019/0304598 A1 | 10/2019 | Hansen et al. |
| 2019/0388183 A1 | 12/2019 | Poirier et al. |

\* cited by examiner

WIRELESSLY DETECTABLE OBJECT THAT EMITS A VARIABLE-FREQUENCY RESPONSE SIGNAL, AND METHOD AND SYSTEM FOR DETECTING AND LOCATING SAME

CROSS-REFERENCE TO RELATED APPLICATIONS

This application claims the benefit of and priority to U.S. Provisional Patent Application Ser. No. 62/741,274 filed Oct. 4, 2018, the entire disclosure of which is incorporated by reference herein.

TECHNICAL FIELD

The present disclosure generally relates to wirelessly detectable objects, and more particularly to wirelessly detectable objects that may emit a variable frequency response signal upon receiving an interrogation signal. Such may be used to mark objects used in medical procedures or may take the form of objects used in medical procedures, for instance sponges, gauze, or instruments.

BACKGROUND

Description of the Related Art

It is often useful or important to be able to determine the presence or absence of an object.

For example, it is important to determine whether objects associated with surgery are present in a patient's body before completing the surgery. Such objects may take a variety of forms, such as, for example, instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures that include checklists or require multiple counts be performed to track the use and return of objects during surgery. Such manual approaches are inefficient, require the time of highly trained personnel, and are prone to error.

Another approach employs automation using wireless transponders and an interrogation unit that may include a transceiver. An automated system may advantageously increase accuracy while reducing the amount of time required of highly trained and highly compensated personnel. Such an approach may employ passive wireless transponders which are attached to various objects used during surgery. The transceiver may emit wireless signals (e.g., radio or microwave frequency) which power the transponders. The transceiver may detect wireless signals returned by the transponders in response. Some implementations employ wireless transponders that store and return a unique identifier. These wireless transponders are often referred to as radio frequency identification (RFID) transponders or tags. Other implementations employ transponders that do not store or return a unique identifier, but rather return (e.g., backscatter) a signal that indicates a presence of the wireless transponder without uniquely identifying the specific wireless transponder. Systems employing dumb wireless transponders typically have better range and, or, ability to detect wireless transponder tagged objects within body tissue as compared to systems employing RFID wireless transponders. Such can be particular advantageous, for instance where a patient is obese. Examples an approach employing dumb wireless transponders are discussed in U.S. Pat. No. 6,026,818, issued Feb. 22, 2000, and U.S. Patent Publication No. US 2004/0250819, published Dec. 16, 2004.

BRIEF SUMMARY

However, some of these approaches do not allow identification of a specific object, for example from a collection of similar objects. For instance, approaches employing dumb wireless transponders typically cannot identify a particular or specific lap sponge from a group of lap sponges. Conventional approaches that allow identification of the object via transmitting an identifier typically transmit a signal at frequencies that have a short range of detection, which may inhibit detection of the transponder, and thus, the object attached thereto. Furthermore, these transponders may not be detectable by the interrogation device when they are situated such that there is an obstacle or membrane, such skin or flesh, between the transponder and the interrogation device. In addition, some of these approaches may be susceptible to interference from noise, which may result in the response signal transmitted from the transponder not being detected by the interrogation unit.

Consequently, a new approach to uniquely identify and robustly detect the presence and absence of a transponder assembly as well as identification is desirable.

A wirelessly detectable object may be summarized as including: at least one antenna; a passive variable-frequency transponder circuit that is communicatively coupled to the at least one antenna, the passive variable-frequency transponder circuit powered by an interrogation signal received via the at least one antenna from an external source, and operable to return a wireless response signal via the at least one antenna, the response signal having a frequency that varies over a single interrogation cycle to produce a characteristic signature in the wireless response signal.

The passive variable-frequency transponder circuit may include at least one inductor and at least one varactor diode, the varactor diode which has a variable capacitance that depends at least in part on a control voltage, the frequency of the wireless response signal which varies based at least in part on the variable capacitance of the varactor diode. The passive variable-frequency transponder circuit may generate a response voltage upon receiving the interrogation signal, the response voltage which decreases when the interrogation signal is removed from the passive variable-frequency transponder circuit, and wherein the control voltage for the variable capacitance in the varactor diode depends at least in part upon the response voltage. The variable capacitance of the varactor diode may vary inversely with the control voltage. The frequency of the wireless response signal may vary inversely with respect to the variable capacitance. The at least one inductor may include a plurality of coils, each coil which extends in a direction different from the directions in which each of the other respective coils extends. Each of the plurality of coils may extend at a right angle with respect to the direction at which each of the other respective coils extends. Each of the plurality of coils may include ferrite. The passive variable-frequency transponder circuit may include at least one inductor, a first capacitor, and a switch, the switch which is operable to selectively electrically couple and decouple at least a second capacitor to the other components of the passive variable-frequency transponder circuit, in which the wireless response signal returned via the antenna has a first frequency when the second capacitor is electrically coupled to the resonant circuit and has a second frequency when the second capacitor is decoupled from the resonant circuit. The second frequency may be lower than the first frequency. The switch may include one or more transistors. The at least one inductor may include a plurality of coils, each coil which extends in a direction different from the directions in which each of the other respective coils extends. Each of the plurality of coils may extend at a right angle with respect to the direction at which each of the other respective coils extends. The at least one antenna may include a first antenna and a second antenna, and wherein the passive variable-frequency transponder circuit includes at least a first resonant circuit that is electrically communicatively coupled to the first antenna, and a second resonant circuit that is communicatively coupled to the first resonant circuit and to the second antenna, wherein the first resonant circuit is powered by the interrogation signal received via the first antenna and generates a first signal of a first frequency in response, wherein the second resonant circuit is powered by the first signal and generates a second signal of a second frequency in response, and wherein the response signal returned by the second antenna includes at least one of the first signal and the second signal. The second antenna may be further communicatively coupled to the first resonant circuit, wherein the response signal returned by the second antenna may include at least the first signal and the second signal. The response signal may include only the second signal. In operation, the first resonant circuit may receive the interrogation signal during a first time period and the second antenna may generate the response signal during a second time period, the first time period which at least partially overlaps with the second time period. The wirelessly detectable object may further include: a pouch with an interior cavity, the passive variable-frequency transponder circuit which is received within the interior cavity of the pouch. The wirelessly detectable object may further include: a piece of absorbent material, wherein the pouch is physically coupled to at least a portion of the piece of absorbent material. The piece of absorbent material may be at least one of a surgical sponge and surgical gauze. The wirelessly detectable object may further include: a piece of absorbent material, the passive variable-frequency transponder circuit which is physically coupled to the piece of absorbent material. The piece of absorbent material may be at least one of a surgical sponge and surgical gauze.

A system to detect a wirelessly detectable object may be summarized as including: the wirelessly detectable object, the wirelessly detectable object which includes at least one antenna; and a passive variable-frequency transponder circuit that is communicatively coupled to the at least one antenna, the passive variable-frequency transponder circuit powered by an interrogation signal received via the at least one antenna from an external source, and operable to return a wireless response signal via the at least one antenna, the response signal having a frequency that varies over a single interrogation cycle to produce a characteristic signature in the wireless response signal; and a transceiver, the transceiver which includes at least one antenna, the least one antenna from the transceiver which emits the interrogation signal and receives the response signal.

The system may further include: a processor that is communicatively coupled to the transceiver, the processor which executes one or more instructions that cause the transceiver to receive the response signal from the at least one antenna in the transceiver and to determine a distance from the transceiver to the wirelessly detectable object based at least in part upon the received response signal. The processor may further determine the distance from the transceiver to the wirelessly detectable object based at least in part upon the emitted interrogation signal. The distance between the transceiver and the wirelessly detectable object may include a distance range. The transceiver may be a wand.

A method of operation of a wirelessly detectable object may be summarized as including: receiving an interrogation signal via at least one antenna from an external source; powering by the interrogation signal a passive variable-frequency transponder circuit that is communicatively coupled to the at least one antenna; and returning by the passive variable-frequency transponder circuit a wireless response signal via the at least one antenna, the wireless response signal having a frequency that varies over a signal interrogation cycle to produce a characteristic signature in the wireless response signal.

The passive variable-frequency transponder circuit may include at least one inductor and at least one varactor diode having a variable capacitance, and wherein powering the passive variable-frequency transponder circuit may include varying the frequency of the wireless response signal based at least upon varying the capacitance of the at least one varactor diode. The passive variable-frequency transponder circuit may include at least one inductor, a first capacitor, and a switch, and wherein powering the passive variable-frequency transponder circuit may include selectively electrically coupling and decoupling at least a second capacitor to the other components of the passive variable-frequency transponder circuit.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
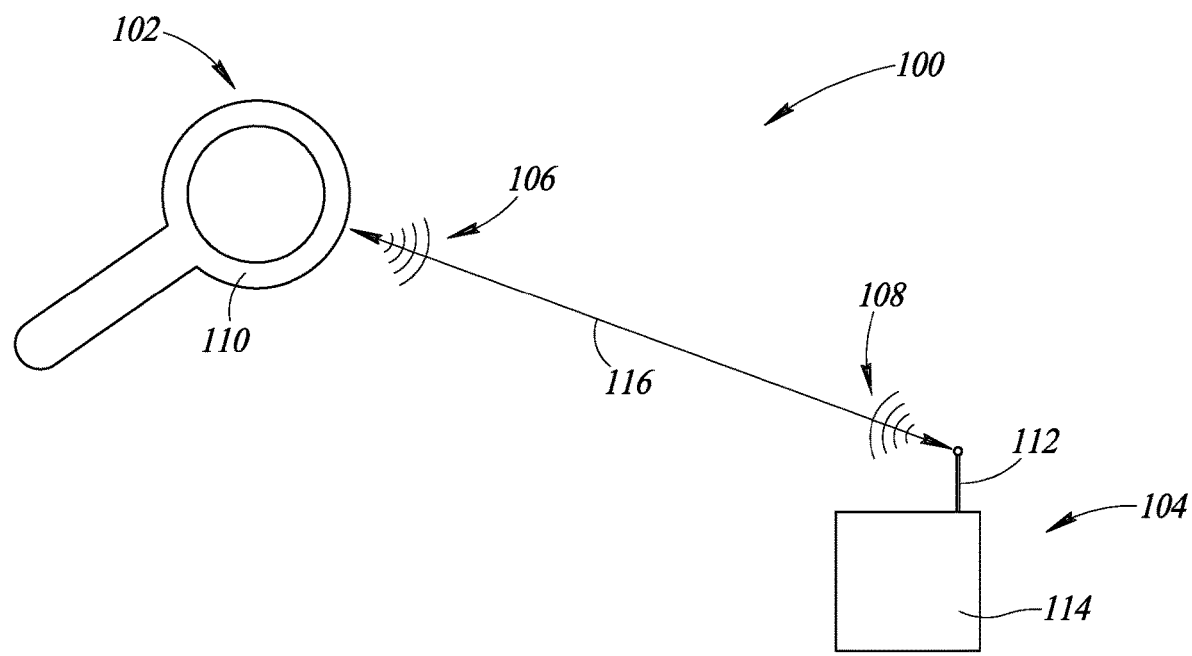
FIG. 1 shows a system that includes a transceiver and a wirelessly detectable object, in which the transceiver may emit an interrogation signal that may be received by the wirelessly detectable object, and the wirelessly detectable object may return in response a variable-frequency response signal, according to at least one illustrated implementation.

FIG. 1 shows a system 100 that includes a transceiver 102 and a wirelessly detectable object 104, in which the transceiver 102 may emit an interrogation signal 106 that is received by the wirelessly detectable object 104, and the wirelessly detectable object 104 may return in response a wireless response signal 108, according to at least one illustrated implementation. In some implementations, the transceiver 102 may receive the wireless response signal 108 returned by the wirelessly detectable object 104 and may perform additional processing on the wireless response signal 108. In some implementations, the transceiver 102 may be comprised of a wand 110 that emits interrogation signals 106 of one or more frequencies that are used to detect wirelessly detectable objects 104 that have been attached or physically coupled to items used in a medical and/or surgical setting. Such items may include, for example, gauze, bandages, medical sponges, medical equipment, or other items that may be used in medical and/or surgical procedures. In such situations, the wand 110 may be used to prevent these items from being lost, or from being left in dangerous or undesirable locations by detecting the respective wirelessly detectable objects 104 attached to such items. In some situations, for example, the wand 110 may be passed over a patient after an operation or other medical procedure to detect any wirelessly detectable objects 104 that are attached to items, such as surgical gauze, bandages, or sponges, used in the medical and/or surgical procedure. Such items, once detected, may be removed from the patient.

The wirelessly detectable object 104 may include an antenna 112 and a passive variable-frequency transponder circuit 114. The antenna 112 may be used to transmit and/or receive wireless signals, and may be communicatively coupled to the passive variable-frequency transponder circuit 114. In some implementations, the interrogation signal 106 emitted by the transceiver 102 may be received by the passive variable-frequency transponder circuit 114 via the antenna 112. The passive variable-frequency transponder circuit 114 may be comprised of one or more circuits such as, for example, tank circuits, LC circuits, RLC circuits, or other types of circuits that may be powered by the interrogation signal 106. As such, the interrogation signal may cause a voltage potential to be generated across the passive variable-frequency transponder circuit 114 when the interrogation signal 106 is received by the passive variable-frequency transponder circuit 114. When the interrogation signal 106 is no longer received by the passive variable-frequency transponder circuit 114, e.g., when the interrogation signal 106 has been turned off or the passive variable-frequency transponder circuit 114 has moved away from the source of the interrogation signal 106, the voltage potential across the passive variable-frequency transponder circuit 114 may begin to decay at a defined rate.

The passive variable-frequency transponder circuit 114 may generate a response signal upon receiving the interrogation signal 106. In some implementations, the response signal generated by the passive variable-frequency transponder circuit 114 may be the wireless response signal 108 that has a frequency that varies with respect to time. In some implementations, the frequency of the wireless response signal 108 may be varied, for example, by changing the value(s) of one or more components (e.g., inductors, capacitors, resistors) in the passive variable-frequency transponder circuit 114. In some implementations, the values of such components may be changed using, for example, a control voltage. As such, a change in the control voltage may result in the frequency of the wireless response signal 108 to increase and/or decrease based upon the corresponding change in value of the one or more components in the passive variable-frequency transponder circuit 114. In some implementations, the control voltage used to change the frequency of the wireless response signal 108 may be related to the voltage generated across the passive variable-frequency transponder circuit 114 by the interrogation signal 106. Because the voltage across the passive variable-frequency transponder circuit 114 changes (e.g., decays) when the interrogation signal 106 is no longer received, the change in this voltage may be used to vary the frequency of the wireless response signal 108. The passive variable-frequency transponder circuit 114 may return the wireless response signal 108 via the antenna 112.

In some implementations, the frequency of the wireless response signal 108 may be varied in other ways. For example, in some implementations, a switch may be used to selectively couple and decouple components (e.g., inductors, capacitors, resistors) within the passive variable-frequency transponder circuit 114. Such selective coupling and de-coupling of components may be used to vary the frequency of the wireless response signal 108 generated by the passive variable-frequency transponder circuit 114.

In some implementations, the variations or changes in the frequency of response signal returned by the wireless response signal 108 may be used to provide a signature for the wirelessly detectable object 104. In some instances, as discussed above for example, the voltage across the passive variable-frequency transponder circuit 114 may decay at a well-defined rate when the interrogation signal 106 is no longer received. As such, the defined decay in the voltage across the passive variable-frequency transponder circuit 114 may result in the corresponding change in the frequency of the wireless response signal 108 to also be well-defined, such that the change in frequency of the wireless response signal 108 may be used to produce a characteristic signature in the wireless response signal 108. Such a characteristic signal may be repeated during each interrogation cycle during which the passive variable-frequency transponder circuit 114 is powered by the interrogation signal 106. In some instances, switches may be used to selectively couple and decouple components within the passive variable-frequency transponder circuit 114. Such selectively coupling and decoupling may be used to generate a characteristic signature for the wireless response signal 108. In some implementations, the transceiver 102 may detect the characteristic signature within the wireless response signal 108. As such, the transceiver 102 may associate the wireless response signal 108 with the wirelessly detectable object 104 and/or may perform additional processing based upon the detected characteristic signature.

In some implementations, the wireless response signal 108 may be used to determine a distance to the wirelessly detectable object 104. For example, in some implementations, the transceiver 102 may detect the wireless response signal 108 emitted by the antenna 112, and use information regarding the wireless response signal 108 to determine a distance 116 between the transceiver 102 and the antenna 112 portion of the wirelessly detectable object 104. Such a determination may be based upon the strength, e.g., power density, of the wireless response signal 108 that is emitted by the antenna 112 when the passive variable-frequency transponder circuit 114 is fully powered. Such a value for the power density may be defined based upon the structure and design of the passive variable-frequency transponder circuit 114. Accordingly, the value for the power density of the wireless response signal 108 emitted by the antenna 112 may have a known value. When the wireless response signal 108 propagates outward from the antenna 112, the power density of the wireless response signal 108 decreases at a known rate. Accordingly, in some implementations, the distance 116 may be determined based upon the known power density of the wireless response signal 108 as emitted by the antenna 112, the known rate at which the power density decreases across distances, and the measured value of the power density of the wireless response signal at the transceiver 102.

As an example, in some implementations, the value of the power density of the wireless response signal 108 at any location may be inversely proportional to the square of the distance between that location and the antenna 112. Accordingly, the transceiver 102 may determine the distance 116 between the antenna 112 and the transceiver 102 by comparing the power density of the wireless response signal 108 received at the transceiver 102 with the known power density of the wireless response signal 108 as emitted by the antenna 112. In some implementations, the distance 116 may be determined according to the following:

$$d = \sqrt{\frac{\rho_{antenna}}{4\pi\rho_{transceiver}}} \qquad \text{Eq. 1}$$

d=Distance 116 between the transceiver 102 and the antenna 112

$\rho_{antenna}$=Power density of wireless response signal 108 at antenna 112 (known)

$\rho_{antenna}$=Power density of wireless response signal 108 received at transceiver 102 (measured)

In some implementations, a distance range between the antenna 112 and the transceiver 102 may be determined. Such a distance range may be based, for example, upon one or more factors, such as tolerance levels for detecting and measuring the power density of the wireless response signal 108 at the transceiver 102, and/or the precision of the power density of the wireless response signal 108 as emitted by the antenna 112. In some implementations, the distance range may be based upon a percentage of the distance 116 as determined based upon measurements at the transceiver 102. Such determinations of the distance and/or distance range may be provided by a processor-enabled component, such as the transceiver 102 and/or any other processor-enabled component that may be communicatively coupled to the transceiver 102.

Figure 2A:
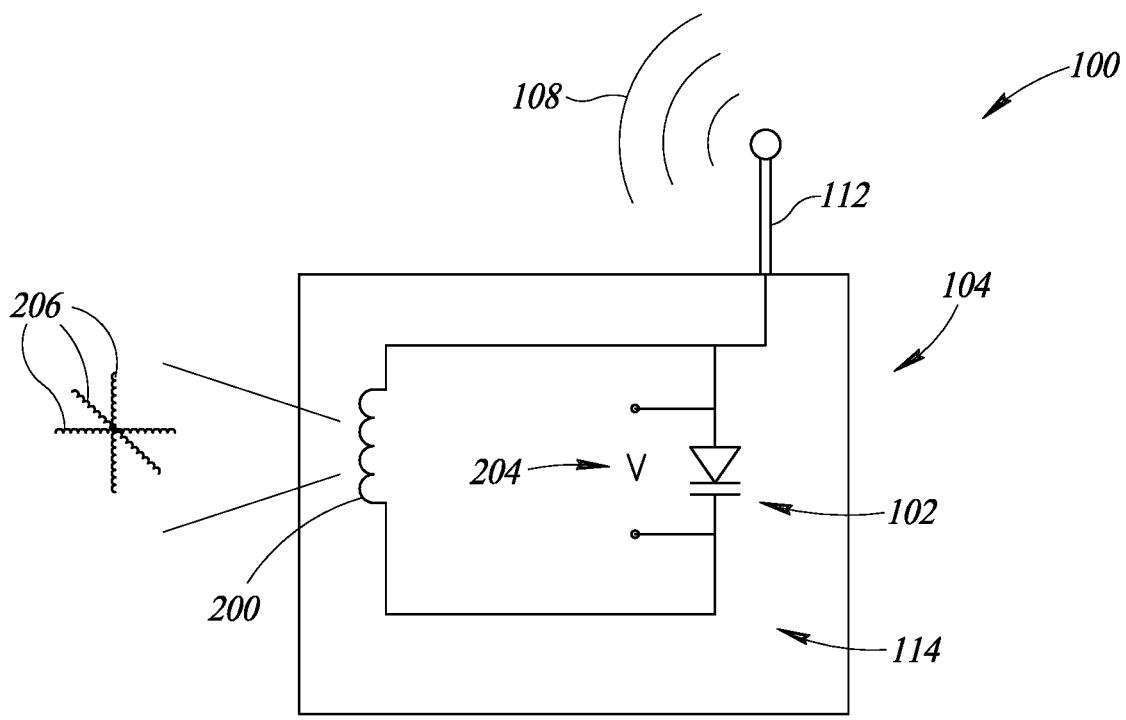
FIG. 2A is a schematic diagram of a wirelessly detectable object that includes an antenna and a passive variable-frequency transponder circuit that includes a varactor diode, according to at least one illustrated implementation.

FIG. 2A shows a wirelessly detectable object 104 that includes an antenna 112 and a passive variable-frequency transponder circuit 114 that includes an inductor 200 and a varactor diode 202, according to at least one illustrated implementation. In such an implementation, the antenna 112 may receive an interrogation signal 106, such as one that may be transmitted by the transceiver 102. Such an interrogation signal 106 may be transmitted via the antenna 112 to the passive variable-frequency transponder circuit 114, which may include the inductor 200 and the varactor diode 202. The varactor diode 202 may function as a variable capacitor in which the capacitance of the varactor diode 202 varies as a function of a control voltage 204. In some implementations, for example, the capacitance of the varactor diode 202 may be based upon the voltage potential across the varactor diode 202, such that this voltage potential controls the value of the capacitance of the varactor diode 202.

In some implementations, the inductor 200 and the varactor diode 202 may form a resonant circuit that is energized when receiving electromagnetic waves of a defined frequency and/or a defined frequency range. In such implementations, the values of the inductor 200 and/or the varactor diode 202 may be chosen such that the passive variable-frequency transponder circuit 114 is energized by the frequency of the interrogation signal 106. Once energized, the passive variable-frequency transponder circuit 114 may generate a response voltage across the passive variable-frequency transponder circuit 114. The response voltage may be used to generate a response signal with a resonant frequency in which the resonant frequency may be based upon the respective values of the components that comprise the passive variable-frequency transponder circuit 114, such as for example, the value of the inductance for the inductor 200 and/or the value of the capacitance of the varactor diode 202.

In some implementations, the response voltage across the passive variable-frequency transponder circuit 114 may provide a control voltage 204 that may be used to control the values of one or more components in the passive variable-frequency transponder circuit 114. For example, in some implementations, the control voltage 204 may be used to control the capacitance of the varactor diode 202. In such implementations, the response voltage in the passive variable-frequency transponder circuit 114 may soon reach a maximum value when the interrogation signal 106 is received, and maintain such a maximum value as long as the antenna 112 receives the interrogation signal 106. As such, the capacitance of the varactor diode 202 may also reach a steady value during this period such that the passive variable-frequency transponder circuit 114 generates a wireless response signal 108 with a steady frequency while the passive variable-frequency transponder circuit 114 is powered by the interrogation signal. When the interrogation signal 106 is no longer present, the control voltage 204 may decay at a defined rate in which the rate of decay may be based, for example, on the value of the varactor diode 202 and/or the value of the inductor 200. As a result, the capacitance of the varactor diode 202 may correspondingly change as the control voltage 204 decays.

The change in the capacitance of the varactor diode 202 may result in the frequency of the wireless response signal 108 also changing. In some instances, for example, the value of the capacitance of the varactor diode 202 may be inversely varied with respect to the control voltage 204 such that the capacitance of the varactor diode 202 increases as the control voltage 204 decays. The resonant frequency of the passive variable-frequency transponder circuit 114 may be inversely proportional to the value of the capacitance of the varactor diode 202 such that the resonant frequency of the wireless response signal 108 generated by the passive variable-frequency transponder circuit 114 decreases as the capacitance of the varactor diode 202 increases.

In some implementations, the inductor 200 may be comprised of one or more rods 206. Such rods 206 may be used to inductively couple the inductor 200 to, for example, the transceiver 102. As such, this electrical coupling of the rods 206 with the transceiver 102 may be used to energize the passive variable-frequency transponder circuit 114. In such an implementation, the one or more rods 206 may be oriented in different directions to improve the overall amount of energy captured by the set of rods 206. In some implementations, for example, the inductor 200 may be comprised of two or three rods 206 in which each rod 206 is at a 90° angle with respect to each of the other rods 206. In such an implementation, the set of rods 206 may be contained within a spherical housing to protect the set of rods 206. The rods 206 may be comprised of any type of material that may be used to inductively couple to another component. For example, in some implementations, one or more of the rods 206 may be comprised of a ferrite rod. In some instance, the ferrite rode may have a conductive coil wrapped about an exterior surface thereof to form an inductor.

Figure 2B:
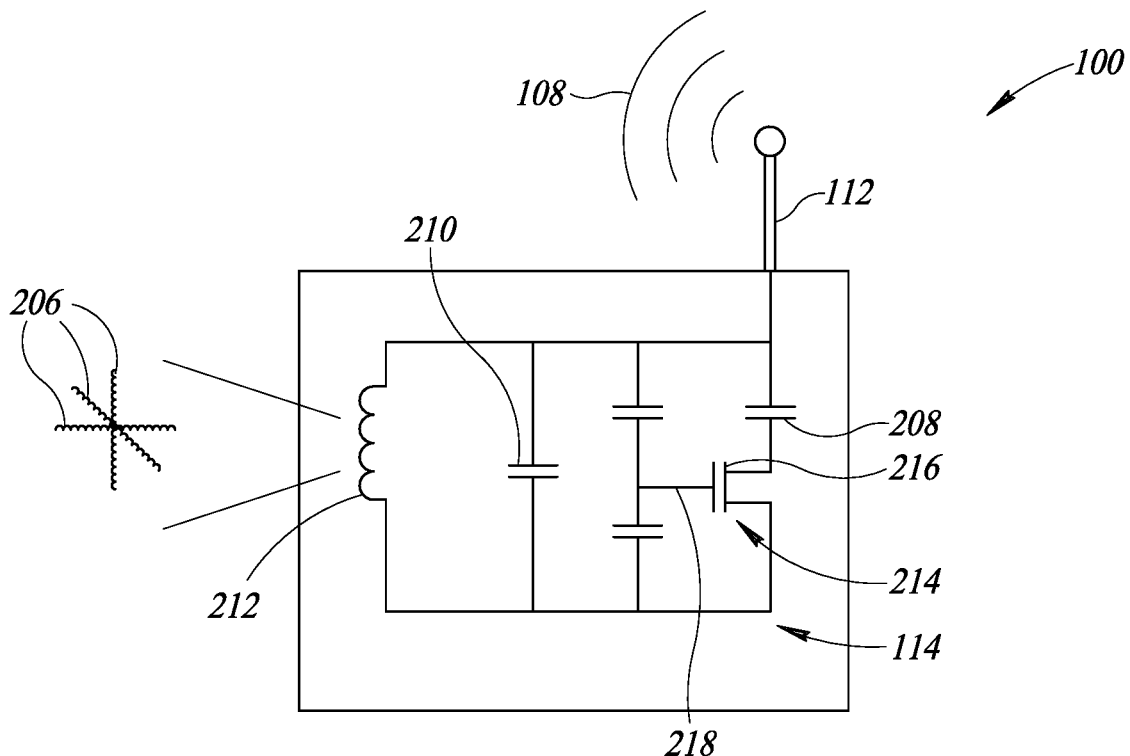
FIG. 2B is a schematic diagram of a wirelessly detectable object that includes an antenna and a variable-frequency transponder circuit that includes a capacitor that may be selectively, electrically coupled to the other components in the wirelessly detectable object, according to at least one illustrated implementation.

FIG. 2B shows a wirelessly detectable object 104 that includes an antenna 112 and a variable-frequency transponder circuit 114 that includes a first capacitor 208 that may be selectively, electrically coupled to the other components in the wirelessly detectable object 104, according to at least one illustrated implementation. In such an implementation, the other components in the passive variable-frequency transponder circuit 114 may include a second capacitor 210 and an inductor 212. When the first capacitor 208 is selectively decoupled from the other components in the passive variable-frequency transponder circuit 114, the other components (e.g., the second capacitor 210 and the inductor) may form a first resonant circuit that generates a response signal having a first frequency and/or frequency range. When the first capacitor 208 is selectively coupled to the other components in the passive variable-frequency transponder circuit 114, the first capacitor 208, the second capacitor 210, and the inductor 212 may form a second resonant circuit that generates a response signal having a second frequency and/or frequency range. In some implementations, the second frequency may be lower than the first frequency.

In some implementations, the first capacitor 208 may be selectively coupled and decoupled to the other components in the passive variable-frequency transponder circuit 114 using a switch 214. In some implementations, the switch 214 may be comprised of one or more transistors 216 that may be controlled by a control voltage 218. Accordingly, the control voltage 218 may be selectively applied to the transistor 216 to maintain the transistor 216 in one of a CLOSED state and an OPEN state. When the transistor 216 is in an OPEN state, the first capacitor 208 is electrically decoupled to the remaining components in the passive variable-frequency transponder circuit 114, resulting in the first resonant circuit having a first resonant frequency. When the transistor 216 is in the CLOSED state, the first capacitor 208 is electrically coupled to the remaining components in the passive variable-frequency transponder circuit 114. In some implementations, the switch 214 may be selectively transitioned between the OPEN state and the CLOSED state in a defined pattern. As such, the defined pattern of switching between the first frequency and the second frequency to generate a response signal that has a characteristic signature. Such a characteristic signature may be detected by the transceiver 102.

In some implementations, the inductor 200 may be comprised of one or more rods 206. Such rods 206 may be used to inductively couple the inductor 200 to, for example, the transceiver 102. As such, this electrical coupling of the rods 206 with the transceiver 102 may be used to energize the passive variable-frequency transponder circuit 114. In such an implementation, the one or more rods 206 may be oriented in different directions to improve the overall amount of energy captured by the set of rods 206. In some implementations, for example, the inductor 200 may be comprised of two or three rods 206 in which each rod 206 is at a 90° angle with respect to each of the other rods 206. In such an implementation, the set of rods 206 may be contained within a spherical housing to protect the set of rods 206. The rods 206 may be comprised of any type of material that may be used to inductively couple to another component. For example, in some implementations, one or more of the rods 206 may be comprised of ferrite.

Figure 3A:
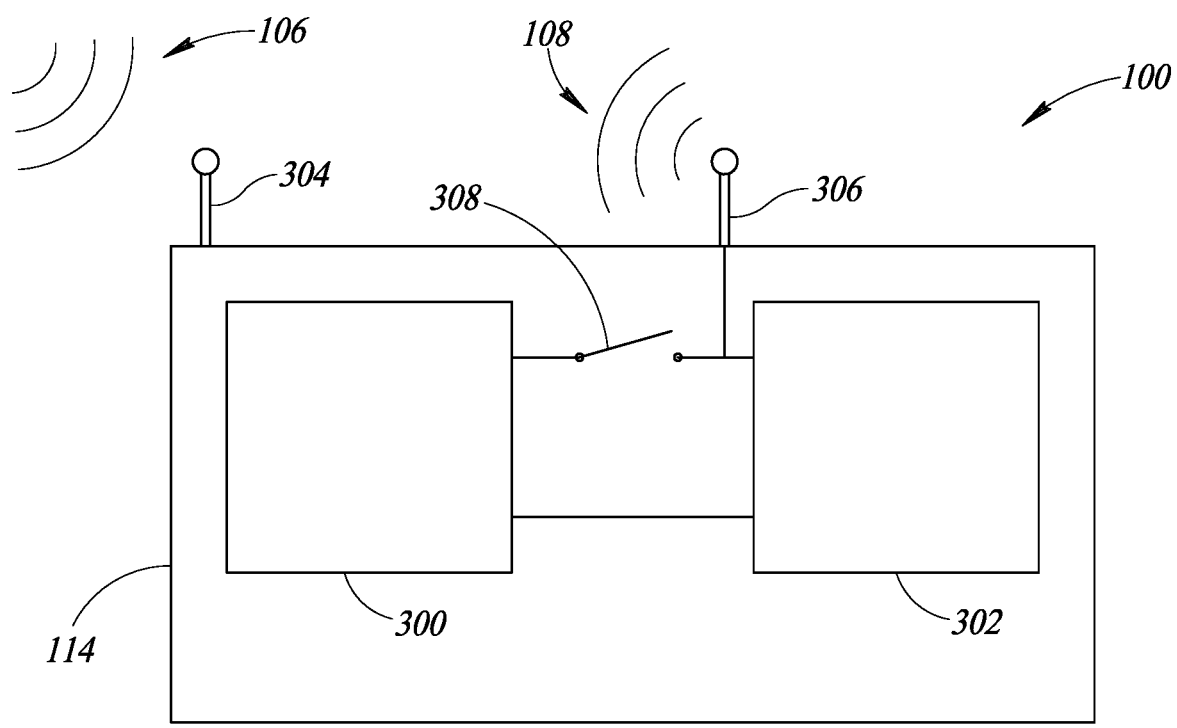
FIG. 3A is a schematic diagram of a wirelessly detectable object that includes a first resonant circuit that is electrically coupled to a second resonant circuit, in which the first resonant circuit is powered by an interrogation signal received via a first antenna, the first resonant circuit provides an output that powers the second resonant circuit, and the second antenna emits a response signal comprised of an output signal received from the second resonant circuit, according to at least one illustrated implementation.

FIG. 3A shows a wirelessly detectable object 104 that includes a first resonant circuit 300 that is electrically coupled to a second resonant circuit 302, in which the first resonant circuit 300 is powered by the interrogation signal 106 received via a first antenna 304, the first resonant circuit 300 provides an output that powers the second resonant circuit 302, and the second antenna 306 emits a wireless response signal 108 comprised of an output signal received from the second resonant circuit 302, according to at least one illustrated implementation. In such an implementation, the passive variable-frequency transponder circuit 114 may include a switch 308 that may be used to selectively couple the first resonant circuit 300 to the second antenna 306. As shown in FIG. 3A, the switch 308 may be in an open position such that the first resonant circuit 300 is decoupled from the second antenna 306. In some implementations, the electrical coupling between the first resonant circuit 300 and the second resonant circuit 302 may include an inductive coupled via, for example, one or more pairs of windings such that power generated in one resonant circuit may be transferred to the other resonant circuit.

In such an implementation, the first resonant circuit 300 may receive the interrogation signal 106 via the first antenna 304. The interrogation signal 106 may power the first resonant circuit 300 when the interrogation signal 106 is received via the first antenna 304. The first resonant circuit 300 may generate a first response signal having a first frequency when powered by the interrogation signal 106. In addition, powering the first resonant circuit 300 may result in the second resonant circuit 302 being powered via, for example, the electrical coupling. When the second resonant circuit 302 is powered, the second resonant circuit 302 may generate a second response signal having a second frequency. The second response signal may be emitted by the second antenna 306 as the wireless response signal 108 from the passive variable-frequency transponder circuit 114. In some implementations, the frequency of the second response signal, and the wireless response signal 108, may be varied as noted above.

As shown in FIG. 3A, the wireless response signal 108 may be emitted by the second antenna 306 simultaneously with the interrogation signal 106 being received at the first antenna 304. As such, the first resonant circuit 300 may be continuously powered by the interrogation signal 106 even while the wireless response signal 108 is emitted by the second antenna 306. Such an implementation may not need to operate with separate discrete time periods to receive the interrogation signal 106 and to emit the wireless response signal 108. Such an implementation may advantageously reduce the amount of time needed to detect the wirelessly detectable object 104.

Figure 3B:
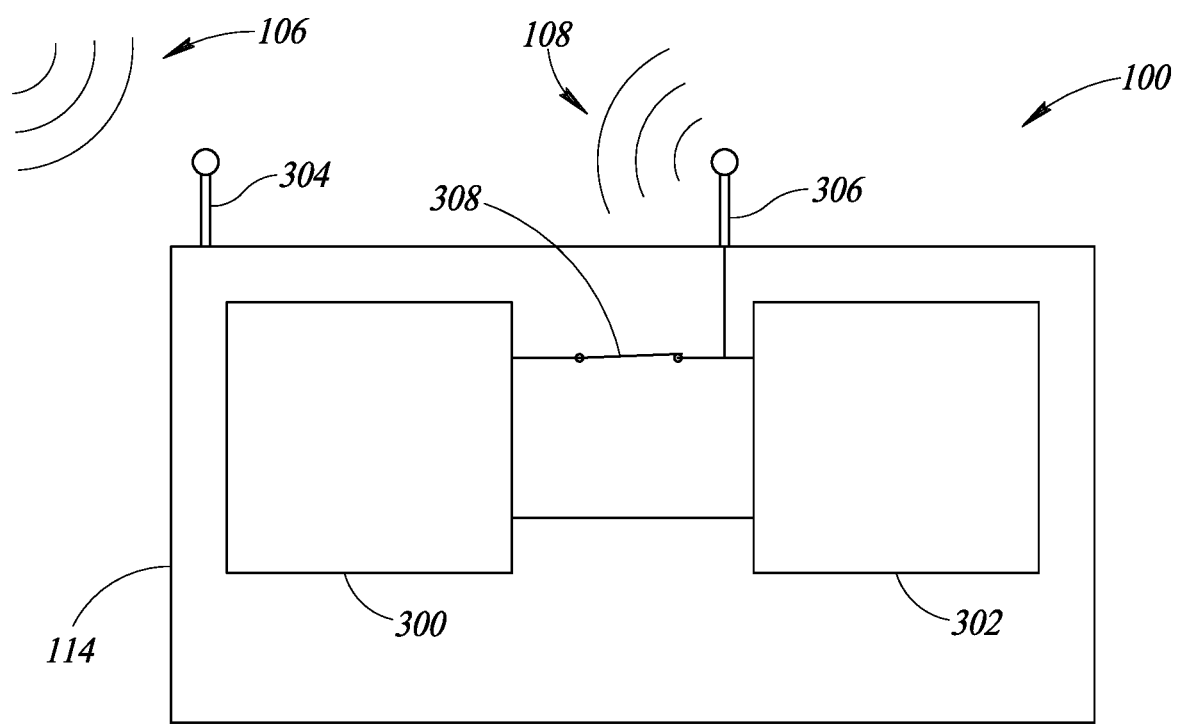
FIG. 3B is a schematic diagram of a wirelessly detectable object that includes a first resonant circuit that is electrically coupled to a second resonant circuit, in which the first resonant circuit is powered by an interrogation signal received via a first antenna, the first resonant circuit provides an output that powers the second resonant circuit, and the second antenna emits a response signal comprised of respective output signals received from the first resonant circuit and the second resonant circuit, according to at least one illustrated implementation.

FIG. 3B shows a wirelessly detectable object 104 that includes the first resonant circuit 300 that is electrically coupled to a second resonant circuit 302, in which the first resonant circuit 300 is powered by the interrogation signal 106 received via the first antenna 304, the first resonant circuit 300 powers the second resonant circuit 302, and the second antenna 306 emits a wireless response signal 108 comprised of respective output signals received from the first resonant circuit 300 and the second resonant circuit 302, according to at least one illustrated implementation. In such an implementation, the switch 308 may be closed in order to selectively couple the first resonant circuit 300 to the second antenna 306. In some implementations, the electrical coupling between the first resonant circuit 300 and the second resonant circuit 302 may include an inductive coupled via, for example, one or more pairs of windings such that power generated in one resonant circuit may be transferred to the other resonant circuit.

In such an implementation, the first resonant circuit 300 may receive the interrogation signal 106 via the first antenna 304. The interrogation signal 106 may power the first resonant circuit 300 when the interrogation signal 106 is received via the first antenna 304. The first resonant circuit 300 may generate a first response signal having a first frequency when powered by the interrogation signal 106. In addition, powering the first resonant circuit 300 may result in the second resonant circuit 302 being powered via, for example, the electrical coupling between the first resonant circuit 300 and the second resonant circuit 302. When the second resonant circuit 302 is powered, the second resonant circuit 302 may generate a second response signal having a second frequency. The second antenna 306 may emit a wireless response signal 108 that is comprised of both the first response signal from the first resonant circuit 300 and the second response signal from the second resonant circuit 302. In such an implementation, the combination of the first resonant circuit 300 and the second resonant circuit 302 may cause the wireless response signal 108 to have a beat. Such a beat may have a distinctive frequency (e.g., a beat frequency) that may be related to the difference between the frequency of the first response signal and the frequency of the second response signal. In some implementations, the beat frequency may advantageously be used to detect the wireless response signal 108. In some implementations, the beat frequency may be used to provide a characteristic signal for the passive variable-frequency transponder circuit 114.

As shown in FIG. 3B, the wireless response signal 108 may be emitted by the second antenna 306 simultaneously with the interrogation signal 106 being received at the first antenna 304. As such, the first resonant circuit 300 may be continuously powered by the interrogation signal 106 even while the wireless response signal 108 is emitted by the second antenna 306. Such an implementation may not need to operate with separate discrete time periods to receive the interrogation signal 106 and to emit the wireless response signal 108. Such an implementation may advantageously reduce the amount of time needed to detect the wirelessly detectable object 104.

Figure 4:
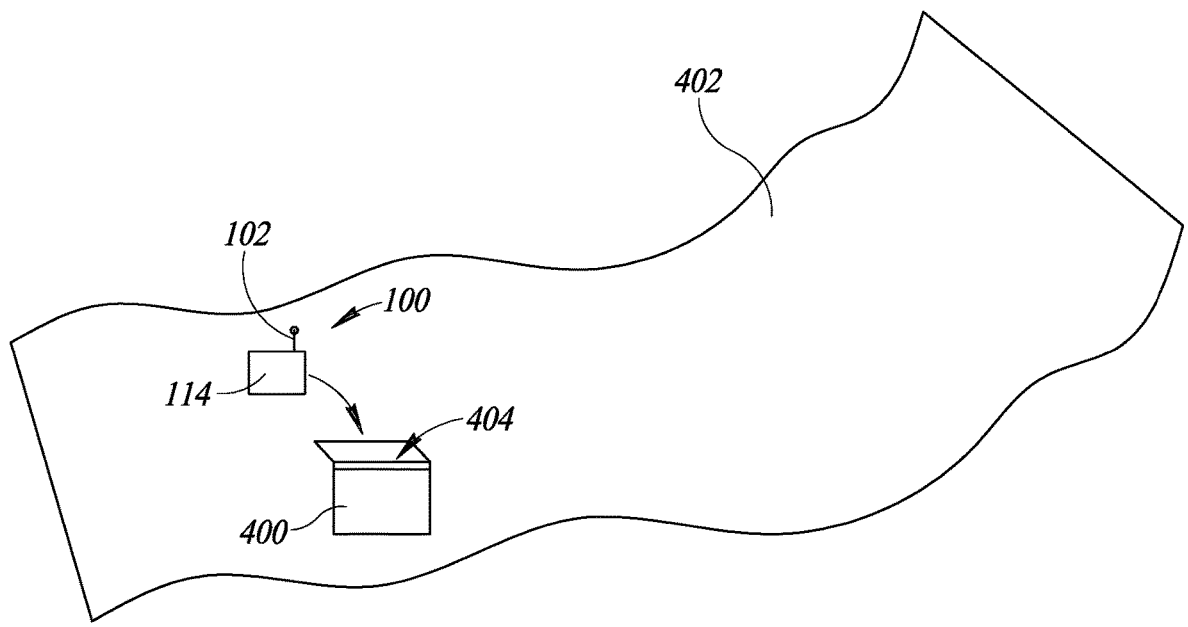
FIG. 4 is a schematic diagram of a pouch that is physically coupled to a piece of absorbent material, in which the pouch includes an interior cavity that may receive at least one wirelessly detectable object, according to at least one illustrated implementation.

FIG. 4 shows a pouch 400 that is physically coupled to a piece of absorbent material 402, in which the pouch 400 includes an interior cavity 404 that may receive at least one wirelessly detectable object 104, according to at least one illustrated implementation. The wirelessly detectable object 104 may be comprised of the antenna 112 and the passive variable-frequency transponder circuit 114. The pouch 400 may take the form of a hollowed rectangle, circle, oval, or other shape to form the interior cavity 401 within a perimeter of the hollowed area. In some implementations, the wirelessly detectable object 104 is freely movable within the interior cavity 401 of the pouch 400. Such may advantageously allow folding, stretching, compression, twisting, or other physical manipulation of the piece of absorbent material 402 without causing damage to the wirelessly detectable object 104. For example, the wirelessly detectable object 104 may freely move within the pouch 400 to an advantageous position experiencing reduced forces. Likewise, the free-floating wirelessly detectable object 104 does not inhibit folding, stretching, compression, twisting, or other physical manipulation of the piece of absorbent material 402, which may be necessary for the surgical procedure.

In some implementations, the pouch 400 includes at least a first flexible layer that forms the interior cavity 404. For example, the first flexible layer can be physically coupled to a surface of the absorbent material 402 to form the interior cavity 404 there between. As another example, the pouch 400 may include a second flexible layer opposite the first flexible layer and physically coupled to the first flexible layer to form the interior cavity 404 there between.

The pouch 400 may include an adhesive layer that may be physically coupled to one or both of the first flexible layer and the second flexible layer. Furthermore, in some implementations, the adhesive layer physically couples the pouch 400 to a piece of absorbent material 402. The adhesive layer may retain structural and adhesive integrity at least at temperatures equal to 121, 130, 132, 136, and/or 150 degrees Centigrade or higher. For example, the adhesive layer may not melt or otherwise liquefy and may retain adhesion to the first flexible layer, second flexible layer and/or the piece of the absorbent material at temperatures less than or equal to 121, 130, 132, 136, and/or 150 degrees Centigrade or higher.

In some implementations, a radio frequency (RF) weld physically couples the first flexible layer to one or both of the second flexible layer and the adhesive layer. Alternatively or additionally to RF weld, adhesives, stitching, clamping, fasteners, or other securing means can physically couple the first flexible layer to the absorbent material 402 or the second flexible layer.

The first and/or second flexible layers and may be fabric laminates or other materials. For example, the first and/or second flexible layers and may be one or more of thermoplastic polyurethane (TPU) and nylon fabric; polyvinyl chloride (PVC) impregnated fabric; layer(s) of PVC, TPU, PET, PETG, LDPE, EVA, open celled polyurethanes, or nylon; other fabrics (e.g., cotton, polyester, leather, vinyl, polyethylene, and blended fabrics); other plastics; or combinations thereof. The flexible layers and are typically relatively thin and may be absorbent or non-absorbent. In some implementations, the flexible layers are of material suitable to prevent entry of fluids into the interior cavity of the pouch 400 (e.g., due to a water-proof or water-resistant coating). Thus, the first and/or second flexible layers and may be soft, pliable, and resistant to ripping or tearing. In one particular example, the first flexible layer includes a first layer of TPU and a first layer of nylon fabric. The second flexible layer includes a second layer of TPU and a second layer of nylon fabric. The TPU layers may be positioned to advantageously allow the first and second layers of TPU to more completely melt together or otherwise physically couple to each other when the RF weld is generated. However, in other implementations, the first and second layers of nylon fabric may be located interior relative to the first and second layers of TPU or may be embedded within the first and second layers of TPU.

In some implementations, the adhesive layer may be a hot melt adhesive layer. In such implementations, the pouch 400 may be constructed at least in part by causing the temperature of at least a portion the hot melt adhesive layer to exceed a melting point temperature associated with the hot melt adhesive layer, thereby causing such portion to at least in part melt. For example, such may be performed using an RF welding machine, planar heat pressing machine, hot-air welding machine, or laminator. Alternatively, the pouch 400 may be baked (e.g., in a chamber) or exposed to various other techniques for applying heat and/or pressure at desired locations. Generally, the melting point temperature will be at least greater than 130 degrees Centigrade. Thus, the adhesive layer may be a pre-formed solid layer that is positioned or laid adjacent to the first and/or the second flexible layers and then caused to at least in part melt and then re-solidify, thereby engaging the first and/or the second flexible layers and resulting in physical coupling therewith. For example, in some implementations, the second layer may be a porous fabric such that the adhesive layer melts through the pores of the fabric to engage the first flexible layer to result in physical coupling of the first flexible layer to the second flexible layer.

The pouch 400 is physically coupleable to the absorbent material 402. For example, the pouch 400 includes an adhesive layer positioned opposite the second flexible layer from the first flexible layer. The adhesive layer may be a hot melt adhesive layer that is meltable to physically couple the pouch 400 to a piece of absorbent material but that has a melting point temperature greater than one or more sterilization temperatures at which common sterilization techniques are performed, thereby permitting the pouch 400 to remain physically coupled to the piece of absorbent material through one or multiple sterilization cycles.

Figure 5:
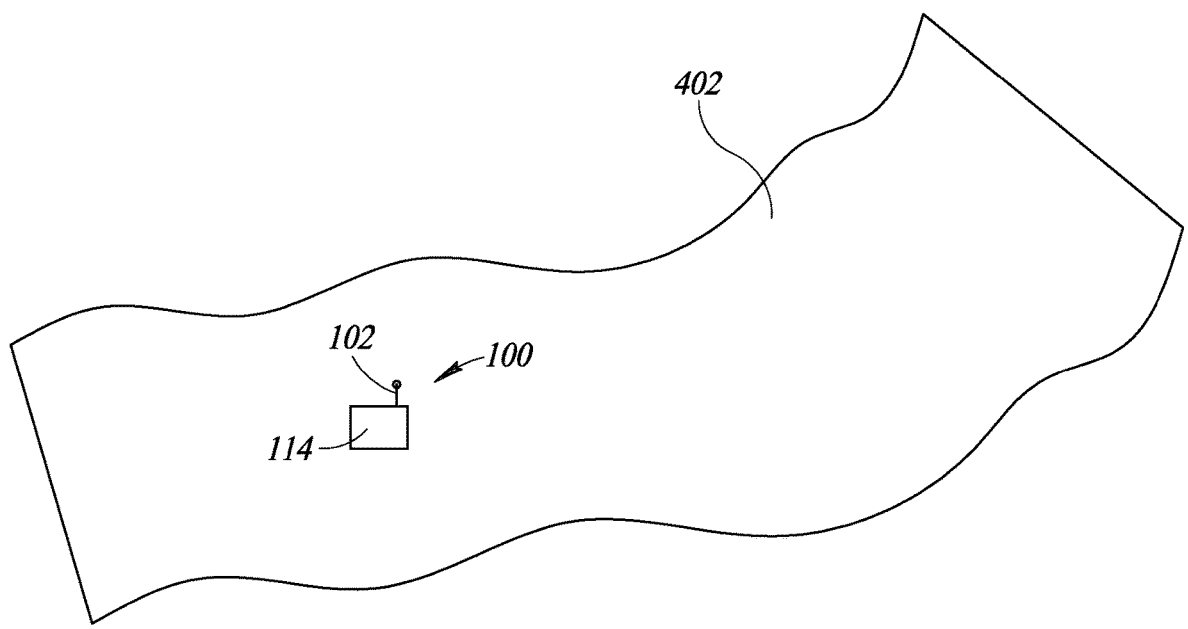
FIG. 5 is a schematic diagram of a wirelessly detectable object that is physically coupled to a piece of absorbent material, according to at least one illustrated implementation.

FIG. 5 shows a wirelessly detectable object 104 that is physically coupled to a piece of absorbent material 402, according to at least one illustrated implementation. Adhesives, stitching, clamping, fasteners, heat sealing, RF welding, or other securing means physically couple the wirelessly detectable object 104 to the piece of absorbent material 402.

The wirelessly detectable object 104 may include an adhesive layer that physically couples the wirelessly detectable object 104 to the piece of absorbent material 402 or other surgical object. The adhesive layer may retain structural and adhesive integrity at least at temperatures equal to 121 degrees Centigrade, 130 degrees Centigrade, 132 degrees Centigrade, 136 degrees Centigrade, and/or 150 degrees Centigrade, or higher. Thus, the adhesive layer may not melt or otherwise liquefy and may retain adhesion to the remainder of the wirelessly detectable object 104 at temperatures less than or equal to 121, 130, 132, 136, and/or 150 degrees Centigrade or higher. In some implementations, the adhesive layer may retain the structural and adhesive integrity at least at temperatures equal to 150 degrees Centigrade or higher.

As an example, the adhesive layer may be a hot melt adhesive layer positioned between the surgical object and the remainder of the wirelessly detectable object 104. In such implementations, the wirelessly detectable object 104 may be physically coupled to the surgical object by causing the temperature of at least a portion the hot melt adhesive layer to exceed a melting point temperature associated with the hot melt adhesive layer, thereby causing such portion to at least in part melt. For example, such may be performed using an RF welding machine, planar heat pressing machine, hot-air welding machine, or laminator. Alternatively, the wirelessly detectable object 104 and the surgical object may be baked (e.g., in a chamber) or exposed to various other techniques for applying heat and/or pressure at desired locations. Generally, the melting point temperature will be at least greater than 121 degrees Centigrade, but may be other temperatures in various implementations.

In contrast to an epoxy that is applied in liquid form and then cured, the adhesive layer of the wirelessly detectable object 104 may be a pre-formed solid layer that is positioned or laid between the remainder of the wirelessly detectable object 104 and the surgical object. The adhesive layer may then be caused to at least in part melt and then re-solidify, thereby engaging the remainder of the wirelessly detectable object 104 and the surgical object and resulting in physical coupling therewith.

In some implementations, the hot melt adhesive layer is a high temperature hot melt adhesive layer (i.e., a hot melt adhesive layer that has a relatively high melting point temperature). For example, the hot melt adhesive layer may have a melting point temperature of greater than 121 degrees Centigrade, greater than 130 degrees Centigrade, greater than 132 degrees Centigrade, or greater than 136 degrees Centigrade. As another example, the hot melt adhesive layer may have a melting point temperature of about 150 degrees Centigrade or higher. The hot melt adhesive layer may have a melting point temperature greater than a sterilization temperature associated with one or more sterilization procedures. For example, the hot melt adhesive layer may have a melting point temperature greater than a steam temperature at which a volume of steam is maintained during one or more steam-based sterilization procedures. For example, two common steam-based sterilization techniques use a volume of steam respectively maintained at 121 degrees Centigrade (250 degrees Fahrenheit) and 132 degrees Centigrade (270 degrees Fahrenheit). The hot melt adhesive layer may have a melting point temperature greater than one or both of such temperatures.

In some implementations, the adhesive layer is biocompatible, permitting use of the wirelessly detectable object 104 in vivo. In some implementations, the adhesive layer is an adhesive web film. In some implementations, the adhesive layer is a thermal lamination film. The adhesive layer may be a meltable plastic layer, such as, for example, a thermoplastic layer.

In some implementations, the adhesive layer may be a thermosetting plastic layer that has an initial cure temperature at which the thermosetting plastic layer cures. For example, the initial cure temperature may be less than 130 degrees Centigrade. Subsequent to curing, the thermosetting plastic layer may retain structural and adhesive integrity at least at temperatures less than or equal to 121, 130, 132, 136, and/or 150 degrees Centigrade or higher.

In some implementations, the adhesive layer may be a heat-activated adhesive layer. Alternatively or additionally, the adhesive layer may be a pressure-activated adhesive layer or a pressure-sensitive adhesive layer. Alternatively or additionally, the adhesive layer may be a water-activated adhesive layer. The adhesive layer may include at least one of thermoplastic polyurethane, silicone, polyamide, polyethersulfone, polyethylene, polypropylene, and ethylene vinyl acetate.

Figure 6:
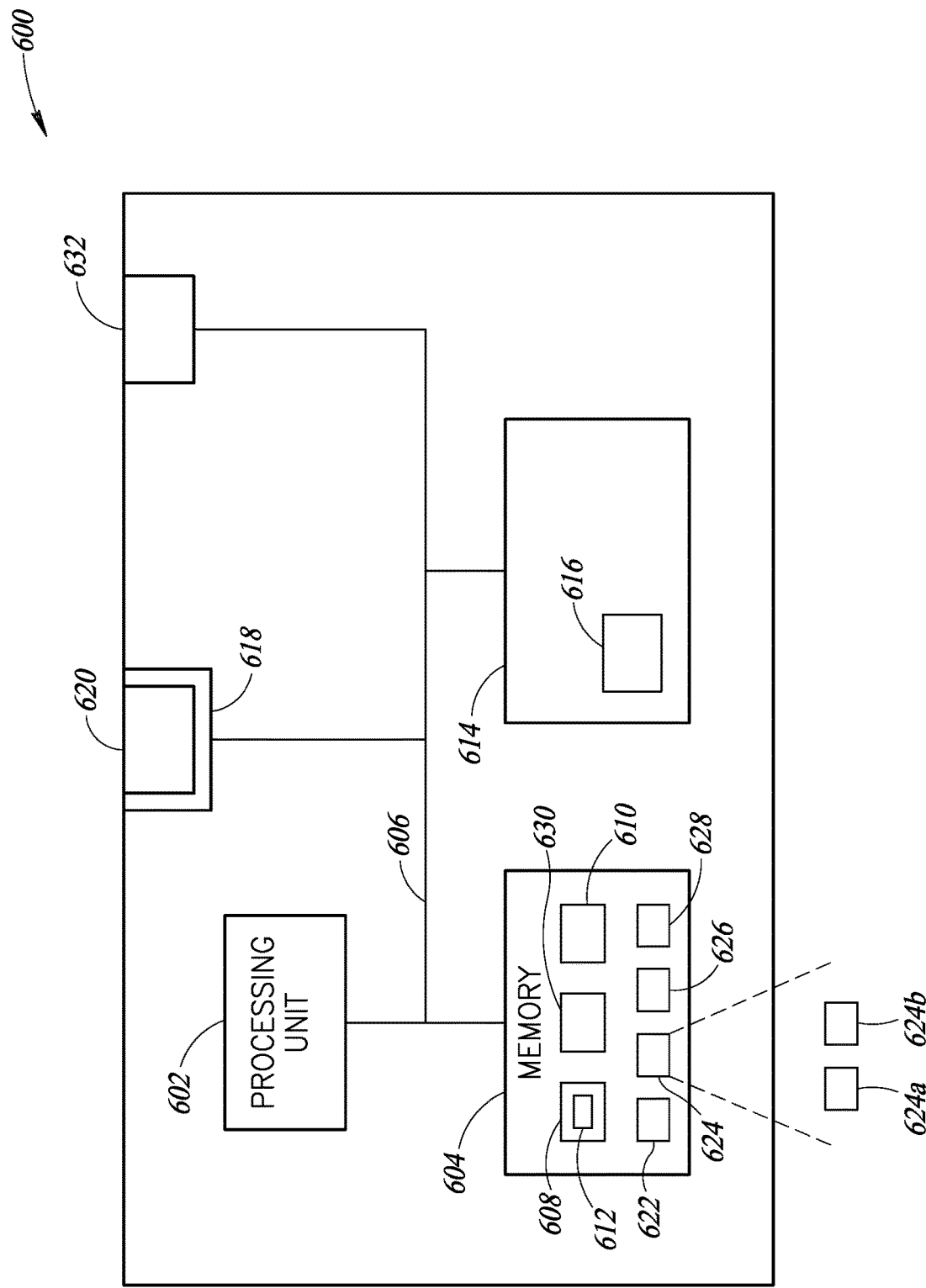
FIG. 6 is a block diagram of a processor-enabled device, according to at least one illustrated implementation.

FIG. 6 shows a processor-enable device 600, according to at least one illustrated implementation. The control system may be used to implement, for example, the transceiver 102, such as the wand 110. The processor-enabled device 600 may take the form of any current or future developed computing system capable of executing one or more instruction sets. The processor-enabled device 600 includes a processing unit 602, a system memory 604, and a system bus 606 that communicably couples various system components including the system memory 604 to the processing unit 602. The processor-enabled device 600 will at times be referred to in the singular herein, but this is not intended to limit the embodiments to a single system, since in certain embodiments, there will be more than one system or other networked computing device involved. Non-limiting examples of commercially available systems include, but are not limited to, an Atom, Pentium, or 80×86 architecture microprocessor as offered by Intel Corporation, a Snapdragon processor as offered by Qualcomm, Inc., a PowerPC microprocessor as offered by IBM, a Sparc microprocessor as offered by Sun Microsystems, Inc., a PA-RISC series microprocessor as offered by Hewlett-Packard Company, an A6 or A8 series processor as offered by Apple Inc., or a 68xxx series microprocessor as offered by Motorola Corporation.

The processing unit 602 may be any logic processing unit, such as one or more central processing units (CPUs), microprocessors, digital signal processors (DSPs), application-specific integrated circuits (ASICs), field programmable gate arrays (FPGAs), programmable logic controllers (PLCs), etc. Unless described otherwise, the construction and operation of the various blocks shown in FIG. 6 are of conventional design. As a result, such blocks need not be described in further detail herein, as they will be understood by those skilled in the relevant art.

The system bus 606 can employ any known bus structures or architectures, including a memory bus with memory controller, a peripheral bus, and a local bus. The system memory 604 includes read-only memory ("ROM") 608 and random access memory ("RAM") 610. A basic input/output system ("BIOS") 612, which can form part of the ROM 608, contains basic routines that help transfer information between elements within the processor-enabled device 600, such as during start-up. Some embodiments may employ separate buses for data, instructions and power.

The processor-enabled device 600 also includes one or more internal nontransitory storage systems 614. Such internal nontransitory storage systems 614 may include, but are not limited to, any current or future developed persistent storage device 616. Such persistent storage devices 616 may include, without limitation, magnetic storage devices such as hard disc drives, electromagnetic storage devices such as memristors, molecular storage devices, quantum storage devices, electrostatic storage devices such as solid state drives, and the like.

The processor-enabled device 600 may also include one or more optional removable nontransitory storage systems 618. Such removable nontransitory storage systems 618 may include, but are not limited to, any current or future developed removable persistent storage device 620. Such removable persistent storage devices 620 may include, without limitation, magnetic storage devices, electromagnetic storage devices such as memristors, molecular storage devices, quantum storage devices, and electrostatic storage devices such as secure digital ("SD") drives, USB drives, memory sticks, or the like.

The one or more internal nontransitory storage systems 614 and the one or more optional removable nontransitory storage systems 618 communicate with the processing unit 602 via the system bus 606. The one or more internal nontransitory storage systems 614 and the one or more optional removable nontransitory storage systems 618 may include interfaces or device controllers (not shown) communicably coupled between nontransitory storage system and the system bus 606, as is known by those skilled in the relevant art. The nontransitory storage systems 614, 618, and their associated storage devices 616, 620 provide nonvolatile storage of computer-readable instructions, data structures, program modules and other data for the processor-enabled device 600. Those skilled in the relevant art will appreciate that other types of storage devices may be employed to store digital data accessible by a computer, such as magnetic cassettes, flash memory cards, RAMs, ROMs, smart cards, etc.

Program modules can be stored in the system memory 604, such as an operating system 622, one or more application programs 624, other programs or modules 626, drivers 628 and program data 630.

The application programs 624 may include, for example, one or more machine executable instruction sets (i.e., detection module 624*a*) capable of detecting one or more wireless response signal 108 transmitted by wirelessly detectable objects 104. The application programs 624 may include, for example, one or more machine executable instruction sets (i.e., distance module 624*b*) capable of detecting the distance between the transceiver 102 and a wirelessly detectable object 104.

In some embodiments, the processor-enabled device 600 operates in an environment using one or more of the network interfaces 632 to optionally communicably couple to one or more remote computers, servers, display devices, and/or other devices via one or more communications channels. These logical connections may facilitate any known method of permitting computers to communicate, such as through one or more LANs and/or WANs. Such networking environments are well known in wired and wireless enterprise-wide computer networks, intranets, extranets, and the Internet.

Figure 7:
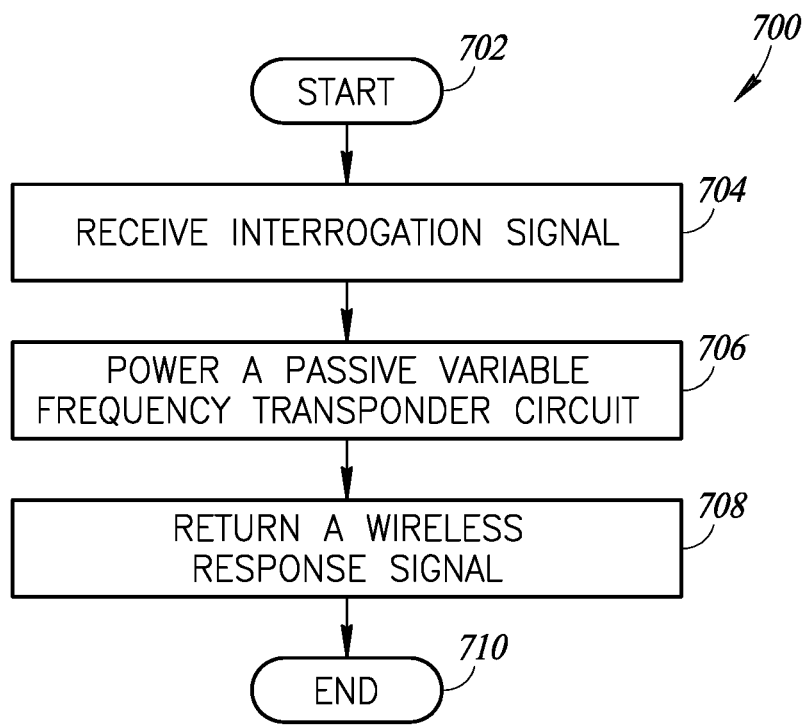
FIG. 7 is a logic flow diagram of a method of operation of a wirelessly detectable object that receives an interrogation signal and emits a variable-frequency response signal, according to at least one illustrated implementation.

FIG. 7 is a logic flow diagram of a method of operation of a wirelessly detectable object that receives an interrogation signal and emits a variable-frequency response signal, according to at least one illustrated implementation. The method 700 can, for example, be executed by one or more wirelessly detectable circuits 102 and may start at 702.

At 704, a wirelessly detectable object 104 may receive an interrogation signal 704 via, for example, one or more antennas (e.g., antenna 112). Such an interrogation signal 704 may be generated by and transmitted from a transceiver 102, such as the wand 110. Such an interrogation signal 106 may be comprised of one or more frequencies, and such frequencies may be used to detect wirelessly detectable objects 104 that have been attached or physically coupled to items, such as items that may be used in a medical and/or surgical setting. These items may include, for example, gauze, bandages, medical sponges, medical equipment, or other items that may be used in medical and/or surgical procedures. In such situations, the interrogation signals 106 emitted by the transceiver 102 may be used to detect the respective wirelessly detectable objects 104 attached to such items so as to prevent these items from being lost, or from being left in dangerous or undesirable locations.

At 706, a wirelessly detectable object 104 may be powered by the received interrogation signal 704. In some implementations, the wirelessly detectable object 104 may include a passive variable-frequency transponder circuit 114 that may be comprised of one or more circuits such as, for example, tank circuits, LC circuits, RLC circuits, or other types of circuits that may be powered by the interrogation signal 106. As such, the interrogation signal may cause a voltage potential to be generated across the passive variable-frequency transponder circuit 114 when the interrogation signal 106 is received by the passive variable-frequency transponder circuit 114. When the interrogation signal 106 is no longer received by the passive variable-frequency transponder circuit 114, e.g., when the interrogation signal 106 has been turned off or the passive variable-frequency transponder circuit 114 has moved away from the source of the interrogation signal 106, the voltage potential across the passive variable-frequency transponder circuit 114 may begin to decay at a defined rate.

At 708, a wirelessly detectable object 104 may return a wireless response signal 108 that has a variable frequency via an antenna (e.g., the antenna 112, and/or the second antenna 306). In some implementations, the wireless response signal 108 may be generated by the passive variable-frequency transponder circuit 114, and the wireless response signal 108 may be emitted by the antenna. In some implementations, the frequency of the wireless response signal 108 may be varied, for example, by changing the value(s) of one or more components (e.g., inductors, capacitors, resistors) in the passive variable-frequency transponder circuit 114 using, for example, a control voltage, as discussed above. As such, a change in the control voltage may result in the frequency of the wireless response signal 108 to increase and/or decrease based upon the corresponding change in value of the one or more components in the passive variable-frequency transponder circuit 114. In some implementations, the frequency of the wireless response signal 108 may be varied in other ways. For example, in some implementations, a switch may be used to selectively couple and decouple components (e.g., inductors, capacitors, resistors) within the passive variable-frequency transponder circuit 114. Such selective coupling and de-coupling of components may be used to vary the frequency of the wireless response signal 108 generated by the passive variable-frequency transponder circuit 114.

At 710, the method 700 terminates, for example until invoked again. Alternatively, the method 700 may repeat continuously or repeatedly, or may execute as multiple instances of a multi-threaded process.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various exemplary methods or processes are described. It is noted that these exemplary methods or processes may include additional acts and/or may omit some acts. In some implementations, the acts of the various exemplary methods or processes may be performed in a different order and/or some acts may be executed or performed concurrently.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Pat. No. 6,026,818, issued Feb. 22, 2000; U.S. Patent Publication No. US 2004/0250819, published Dec. 16, 2004; U.S. Pat. No. 8,710,957, issued Apr. 29, 2014; U.S. Pat. No. 7,898,420, issued Mar. 1, 2011; U.S. Pat. No. 7,696,877, issued Apr. 13, 2010; U.S. Pat. No. 8,358,212, issued Jan. 22, 2013; U.S. Pat. No. 8,111,162, issued Feb. 7, 2012; U.S. Pat. No. 8,354,931, issued Jan. 15, 2013; U.S. Patent Publication No. US 2010/0108079, published May 6, 2010; U.S. Patent Publication No. US 2010/0109848, published May 6, 2010; U.S. Patent Publication No. US 2011/0004276, published Jan. 6, 2011; U.S. Patent Publication No. US 2011/0181394, published Jul. 28, 2011; U.S. Patent Publication No. US 2013/0016021, published Jan. 17, 2013; PCT Patent Publication No. WO 2015/152975, published Oct. 8, 2015; U.S. Provisional patent application Ser. No. 62/143,726 filed Apr. 6, 2015; U.S. Provisional patent application Ser. No. 62/182,294 filed Jun. 19, 2015; U.S. Provisional patent application Ser. No. 62/164,412 filed May 20, 2015; U.S. Non-Provisional patent application Ser. No. 14/523,089 filed Oct. 24, 2014; U.S. Non-Provisional patent application Ser. No. 14/327,208 filed Jul. 9, 2014; U.S. Non-Provisional patent application Ser. No. 15/003,515 filed Jan. 21, 2016; U.S. Non-Provisional patent application Ser. No. 15/003,524 filed Jan. 21, 2016; U.S. Non-Provisional patent application Ser. No. 15/052,125 filed Feb. 24, 2016; U.S. Non-Provisional patent application Ser. No. 15/053,965 filed Feb. 25, 2016; U.S. Provisional patent application Ser. No. 62/360,864 filed Jul. 11, 2016 and entitled "METHOD AND APPARATUS TO ACCOUNT FOR TRANSPONDER TAGGED OBJECTS USED DURING CLINICAL PROCEDURES, EMPLOYING A SHIELDED RECEPTACLE"; U.S. Provisional patent application Ser. No. 62/360,866 filed Jul. 11, 2016 and entitled "METHOD AND APPARATUS TO ACCOUNT FOR TRANSPONDER TAGGED OBJECTS USED DURING CLINICAL PROCEDURES EMPLOYING A SHIELDED RECEPTACLE WITH ANTENNA"; and U.S. Provisional patent application Ser. No. 62/360,868 filed Jul. 11, 2016 and entitled "METHOD AND APPARATUS TO ACCOUNT FOR TRANSPONDER TAGGED OBJECTS USED DURING CLINICAL PROCEDURES, FOR EXAMPLE INCLUDING COUNT IN AND/OR COUNT OUT AND PRESENCE DETECTION", are each incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A wirelessly detectable object, the wirelessly detectable object comprising:
 at least one antenna; and
 a passive variable-frequency transponder circuit that is communicatively coupled to the at least one antenna, the passive variable-frequency transponder circuit powered exclusively by an interrogation signal received via the at least one antenna from an external source, and operable to return a wireless response signal via the at least one antenna,
  wherein a voltage across the passive variable-frequency transponder circuit is configured to decay in a well-defined manner such that the corresponding change in frequency produces a characteristic signature in the wireless response signal, and
  wherein the passive variable-frequency transponder circuit includes at least one inductor and at least one varactor diode, the varactor diode which has a variable capacitance that depends at least in part on a control voltage, the frequency of the wireless response signal which varies based at least in part on the variable capacitance of the varactor diode.

2. The wirelessly detectable object of claim 1 wherein the passive variable-frequency transponder circuit generates a response voltage upon receiving the interrogation signal, the response voltage which decreases when the interrogation signal is removed from the passive variable-frequency transponder circuit, and wherein the control voltage for the variable capacitance in the varactor diode depends at least in part upon the response voltage.

3. The wirelessly detectable object of claim 1 wherein the variable capacitance of the varactor diode varies inversely with the control voltage.

4. The wirelessly detectable object of claim 3 wherein the frequency of the wireless response signal varies inversely with respect to the variable capacitance.

5. The wirelessly detectable object of claim 1 wherein the at least one inductor is comprised of a plurality of coils, each coil which extends in a direction different from the directions in which each of the other respective coils extends.

6. The wirelessly detectable object of claim 5 wherein each of the plurality of coils extends at a right angle with respect to the direction at which each of the other respective coils extends.

7. The wirelessly detectable object of claim 5 wherein each of the plurality of coils is comprised of ferrite.

* * * * *